United States Patent
Vennerstrom

(10) Patent No.: US 6,897,334 B2
(45) Date of Patent: May 24, 2005

(54) PRODUCTION OF CREATINE ESTERS USING IN SITU ACID PRODUCTION

(75) Inventor: Jonathan Vennerstrom, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 10/647,825

(22) Filed: Aug. 25, 2003

(65) Prior Publication Data

US 2005/0049428 A1 Mar. 3, 2005

(51) Int. Cl.$^7$ .............................................. C07C 229/00
(52) U.S. Cl. ...................................................... 560/169
(58) Field of Search ................................. 560/169, 168

(56) References Cited

FOREIGN PATENT DOCUMENTS

WO         02/22135        3/2002

OTHER PUBLICATIONS

Mold, J.D., et al., "Creatine ethyl ester", J. Amer. Chem. Soc. 77: 178–180 (1955).

Nudelman, A., et al., "Acetyl chloride–methanol as a convenient reagent for: a) Quantitative formation of amine hydrochlorides b) carboxylate ester formation c) mild removal of N–t–BOC–protective group", Synth. Comm. 28: 471–474 (1998).

Dox, A., et al., "Esterification of creatine", J. Biol. Chem., 54: 671–673 (1922).

*Primary Examiner*—Paul A. Zucker
(74) *Attorney, Agent, or Firm*—Dann, Dorfman, Herrell & Skillman, P.C.

(57) ABSTRACT

Methods are provided for the improved production of a creatine ester by in situ production of an acid catalyst.

17 Claims, 2 Drawing Sheets

PRODUCTION OF CREATINE ESTERS USING IN SITU ACID PRODUCTION

FIELD OF THE INVENTION

The present invention relates to improvements in the production of creatine esters by in situ production of an acid catalyst for the esterification reaction.

BACKGROUND OF THE INVENTION

Creatine is an endogenous nutrient produced naturally by the liver and kidneys in most vertebrates. The uses of creatine are many, including use as a supplement to increase muscle mass and enhance muscle performance as well as in emerging applications in the treatment of various disorders (see, e.g., WO 02/22135) such as, without limitation, Parkinson's disease (Matthews, R. T., et al., (1999) Exp. Neurol., 157:142–149), Huntington's disease, various neuromuscular Disorders (Klivenyi, P., et al. (1999) Nat. Med., 5:347–350), hypoxia and ishemic brain diseases such as stroke (Balestrino, M., et al. (1999) Brain Res., 816:124–130; Dechent, P., et al. (1999) Am. J. Physiol. 277:R698–R704), various muscular dystrophies (Felber, S., et al. (2000) Neurol. Res., 22:145–150; Willer, B., et al. (2000) Rheumatology, 39:293–298; Rawson, E. S. and Clarkson, P. M. (2000) Int. J. Sports Med., 21:71–75), various skin disorders (U.S. patent application Ser. No. 09/852,966) and heart disease (Gordon, A., et al. (1995) Cardiovasc. Res., 30:413–418; Earnest, C. P., et al. (1996) Clin. Sci., 91:113–118). Creatine may also be used as an anti-inflammatory agent (U.S. patent application No. 10/365,666; Khanna, N. K. and Madan, B. R. (1978) Arch. Int. Pharmacodyn. Ther., 231:340–350). Notably, local administration of creatine can be achieved by absorption through the skin (U.S. Pat. No. 6,413,552; WO 96/33707).

Typically, creatine is taken up into muscle cells by specific receptors and converted to phosphocreatine by creatine kinase. Muscle cells, including skeletal muscle and the heart muscle, function by utilizing cellular energy released from the conversion of adenosine triphosphate (ATP) to adenosine diphosphate (ADP). The amount of phosphocreatine in the muscle cell determines the amount of time it will take for the muscle to recover from activity and regenerate ATP. Phosphocreatine is a rapidly accessible source of phosphate required for regeneration of ATP and sustained use of the muscle.

For example, energy used to expand and contract muscles is supplied from ATP. ATP is metabolized in the muscle by cleaving a phosphate radical to release energy needed to contract the muscle. Adenosine diphosphate (ADP) is formed as a byproduct of this metabolism.

The most common sources of ATP are from glycogen and creatine phosphate. Creatine phosphate is favored as a ready source of phosphate because it is able to resynthesize ATP at a greater rate than is typically achieved utilizing glycogen. Therefore, increasing the amount of creatine in the muscle increases the muscle stores of phosphocreatine and has been proven to increase muscle performance and increase muscle mass.

However, creatine itself is poorly soluble in an aqueous solution (about 10–15 mg/ml). Further, creatine is not well absorbed from the gastrointestinal (GI) tract. Indeed, creatine has been estimated to have a 14% or less absorption rate from the GI tract. Creatine also has low oral bioavailability due, in part, to 1) low lipophilicity and therefore poor membrane permeability, and 2) rapid conversion to creatinine in the acidic environment of the stomach (Edgar and Shiver, J. Amer. Chem. Soc., 47:1179–1188, 1925). Thus, current products require administration of large amounts (typically 5 grams or more) of creatine in order to be effective, which causes such side effects as bloating, gastrointestinal (GI) distress, diarrhea, and the like.

These shortcomings and side effects can be avoided by the administration of creatine esters, which are converted into creatine by esterases found in a variety of cells and biological fluids (see, e.g., WO 02/22135). Creatine esters, such as creatine ethyl ester, are more water soluble (over 200 mg/ml) and lipophilic than creatine and therefore have a greater bioavailability. Additionally, the carboxylic acid functional group of creatine is masked through esterification in creatine esters, thereby preventing the formation of the undesired product creatinine.

It is known that creatine esters can be formed via an acid catalyzed reaction between creatine and suitable alcohols, such as methanol, ethanol, and the like.

Current protocols for generating creatine esters employ an external source of hydrogen chloride acid (HCl), such as compressed, caustic HCl gas, in the esterification of anhydrous creatine (see, e.g., Dox and Yoder, J. Biol. Chem., 67:671–673, 1922). The requirement for compressed, caustic HCl gas, however, complicates production of creatine esters and causes the rapid (and ultimately costly) corrosion of metals used in the system and the surrounding area. Additionally, the use of compressed cylinders of HCl gas introduces significant safety risks and renders adding stoichiometric amounts of the acid difficult.

Clearly, a need exists for a process capable of more efficiently and effectively producing creatine esters.

SUMMARY OF THE INVENTION

In accordance with the present invention, methods are provided for the improved production of a creatine ester involving in situ production of an acid catalyst, preferably HCl.

In one embodiment of the invention, the method of producing an ester of creatine and a lower alcohol comprises the steps of providing a reaction medium comprising creatine and the lower alcohol and heating the reaction medium in the presence of an acid catalyst generated in situ, at a temperature between about 35° C. and about 50° C. to yield the desired ester. Particularly satisfactory results are obtainable when the heating step is carried out at a temperature in the range of about 35° C. to about 40° C.

In carrying out the method of this invention, the acid catalyst is generated by the addition of an acyl halide to the reaction medium. In a particular embodiment, the lower alcohol is ethanol and the acyl halide is acetyl chloride. In another embodiment, the lower alcohol is denatured ethanol comprising about 95% ethanol and 5% ethyl acetate.

In yet another embodiment of the invention, the creatine ester is purified from the reaction medium after formation.

DETAILED DESCRIPTION OF THE INVENTION

In accordance with the present invention, methods for the improved production of creatine ethyl ester by in situ production of HCl are provided.

The following definitions are provided to facilitate an understanding of the present invention:

Creatine ([α-Methylguanido]acetic acid) may be represented by the following formula:

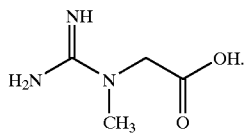

Creatine esters may be represented by the following formula, wherein R is a hydrocarbyl group:

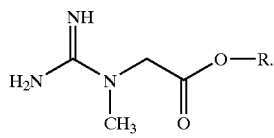

Creatine ethyl ester may be represented by the following formula:

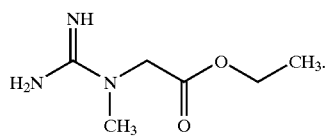

The term "hydrocarbyl", as used herein, refers to an unsubstituted or substituted hydrocarbon radical containing from about 1 to 25 carbon atoms, which may be a straight, branched, or cyclic hydrocarbon group. When substituted, hydrocarbyl groups may be substituted at any available point of attachment. Exemplary unsubstituted groups include alkyls such as methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, octadecyl, nonadecyl, eicosyl, heneicosyl, docosyl, tricosyl, tetracosyl, pentacosyl, and the like; aryls such as phenyl, tolyl, xylyl, napthyl, biphenyl, tetraphenyl, and the like; aralkyls such as benzyl, phenethyl, phenpropyl, phenbutyl, phenhexyl, napthoctyl, and the like; and cycloalkyls such as cyclopropyl, cyclobutyl, cyclohexyl, cycloheptyl, cyclooctyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), carbonyl (—C(=O)), epoxy, alkyloxycarbonyl (—C(=O)—OR), alkylcarbonyloxy (—OC(=O)—R), amino (—$NH_2$), carbamoyl ($NH_2C$(=O)— or NHRC(=O)—), urea (—$NHCONH_2$), alkylurea (—NHCONHR) or thiol (—SH), wherein R in the aforementioned substituents represents a hydrocarbyl radical. Hydrocarbyl groups (moieties) as defined herein may also comprise one or more carbon to carbon double bonds or one or more carbon to carbon triple bonds (i.e., the hydrocarbyl groups may be unsaturated). Hydrocarbyl groups may also be interrupted with at least one oxygen, nitrogen, or sulfur atom.

The terms "halogen," "halo," and "halide" refer to chlorine, bromine, fluorine or iodine.

The term "lower alcohol" refers to aliphatic alcohols having about 1 to 4 carbon atoms such as, without limitation, methanol, ethanol, propanol, butanol, and isopropanol. These lower alcohols may be used singly or in admixture containing two or more such alcohols.

The term "acyl halide" refers to a compound of the formula R—C(=O)—X, wherein R is a hydrocarbyl group, as defined above, and X is a halogen.

Figure 1:
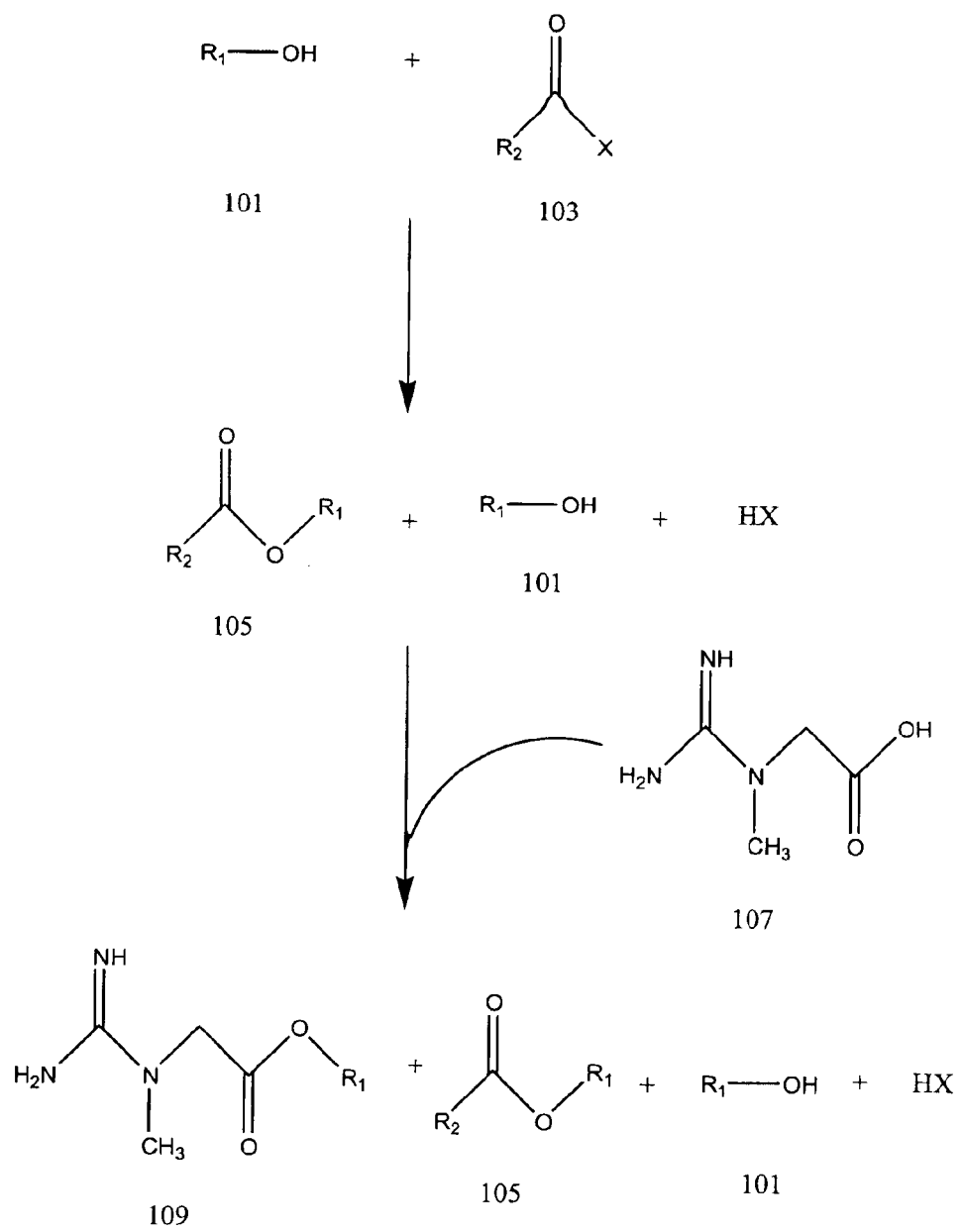
FIG. 1 is an illustration of a reaction scheme for the production of a creatine ester from creatine in accordance with this invention. $R_1$ and $R_2$ are hydrocarbyl groups and X is halogen. $R_1$ and $R_2$ can be the same or different.

The chemical reactions utilized to make creatine esters in accordance with the present invention are depicted in FIG. 1. An acidified alcohol is generated by reacting an excess of an alcohol (101), preferably a lower alcohol, with an acyl halide (103). The lower alcohol is preferably selected from the group consisting of anhydrous ethanol and denatured ethanol such as SDA 35-A (95.75% ethanol; 4.25% ethyl acetate). The acyl halide is preferably an acyl chloride and more preferably acetyl chloride.

The invention is described hereinbelow in terms of using ethanol as the reaction medium and acetyl chloride for the in situ generation of HCl. It should be understood, however, that the instant invention encompasses the use of any acyl halide and alcohol.

One advantage of generating HCl via the reaction of acetyl chloride and ethanol is the formation of ethyl acetate (species of 105 in FIG. 1) which is a non-toxic and volatile solvent which can therefore be readily removed (Nudelman, A., et al. (1998) Synth. Comm., 28:471–474). Additionally, any acetic anhydride or acetic acid impurities in the acetyl chloride are also converted into ethyl acetate during the addition of the acetyl chloride to the ethanol.

The reaction of ethanol with acetyl chloride is beneficially performed with about 1.4–2.0 mole equivalents of acetyl chloride relative to creatine. As noted in Example 2, employing less than about 1.4 mole equivalents of acetyl chloride promotes formation of creatine HCl and not the desired creatine ester product. Additionally, employing more than about 2.0 mole equivalents of acetyl chloride promotes formation of the undesired creatinine HCl reaction byproduct. Particularly satisfactory results may be obtained by employing about 1.5–1.6 mole equivalents of acetyl chloride.

Additionally, the reaction of a lower alcohol and an acyl halide can be performed by the dropwise addition of the acyl halide to the lower alcohol. Preferably, the reaction mixture does not exceed about 60° C. so as to maintain the solubility of the HCl formed in situ and prevent its escape, e.g., by evaporation.

The acidified alcohol can be allowed to cool to below about 50° C., more preferably to about 35 to 40° C. Creatine (107) may then be added to the cooled acidified alcohol. While anhydrous creatine is depicted in FIG. 1, a variety of creatine-containing starting materials, such as creatine monohydrate, may be employed in practicing this invention. As noted above, the acetyl chloride employed to generate the acidified alcohol is about 1.4 to 2.0 mole equivalents of the creatine to be added and the lower alcohol is in excess. Satisfactory results may be obtained when the ratio of creatine to the lower alcohol is about 1 gram creatine: 6 to 10 ml lower alcohol.

Figure 2:
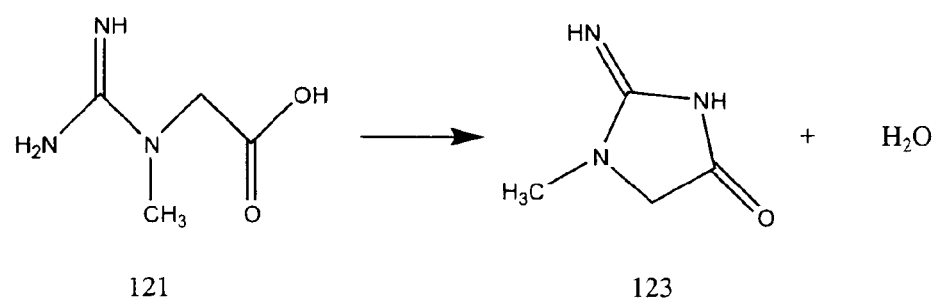
FIG. 2 shows the conversion of creatine to creatinine.

The reaction of the acidified alcohol and creatine can be heated to about 35° C. to 50° C. to promote efficient conversion to the creatine ester (109). While increasing the reaction temperature to greater than 50° C. would tend to cause a more rapid esterification of creatine, the undesired reaction product, creatinine HCl, is produced in a larger proportion. Creatinine HCl is generated by the completion of the cyclization reaction of creatine (see FIG. 2). Importantly, once creatinine HCl is formed, it cannot be converted to the desired product, creatine ester HCl (Mold, J. D., et al. (1955) J. Amer. Chem. Soc. 77:178–180). Therefore, temperature control of the reaction within the above-mentioned range is essential to avoid the production of the "dead-end" product creatinine HCl, while maintaining efficient production of creatine ester HCl in a reasonable time.

Creatine esters generated by the reaction of creatine with acidified alcohol may be purified by methods such as, without limitation, crystallization and flash column chromatography. In one embodiment of the invention, the reaction mixture containing the formed creatine ester is cooled to a range of about 5° C. to 30° C. to allow for the crystallization of the reaction product. Cooling to lower temperatures increase the yields of creatine ester while cooling to higher temperatures within the range increases the purity of the reaction product.

The creatine ester can then be collected by vacuum filtration and can also be washed with ice-cold ethanol, typically about 1 ml per 1 g of starting creatine employed. The reaction product may then be dried in vacuo after most of the solvent has been removed by vacuum filtration. Additionally, the reaction product can be further purified of creatine and creatinine HCl salts and other contaminants by additional rounds of crystallization from warm (35–60° C.) ethanol.

As indicated in the following examples, certain reaction schemes result in a significant portion of the desired creatine ester product remaining in the filtrate. Therefore, further recrystallization, for example, from the filtrate may be advantageous to increase the overall yield of the reaction.

The structure and purity of the creatine ester may be confirmed by, without limitation, HPLC (high performance liquid chromatography), $^1H$ and $^{13}C$ nuclear magnetic resonance (NMR), IR (infrared), melting point and elemental analysis.

The following examples present further detail regarding the practice of the instant invention. These examples are provided for illustrative purposes only and are not intended to limit the scope of the invention in any way.

EXAMPLE 1

Synthesis of Creatine Ethyl Ester Hydrochloride by Acid-Catalyzed Esterification of Creatine Monohyrdate A 1.5 molar equivalent of acetyl chloride was added dropwise to either anhydrous ethanol protected by a calcium chloride drying tube with constant stirring. The acetyl chloride was added at such a rate so as to prevent the temperature of the acidified solvent from exceeding 60° C.

The temperature of the acidified ethanol was then allowed to decline to about 35 to 40° C. When the acidified ethanol reached the lower temperatures, creatine monohydrate was added in one portion in the ratio of 1 g of creatine monohydrate to 6 to 10 ml of acidified ethanol. The resultant reaction was stirred for 2 to 8 hours at about 40 to 50° C.

The temperature of the reaction mixture was then allowed to cool to about room temperature with constant stirring. White crystalline creatine ethyl ester hydrochloride (CEE HCl) was collected by vacuum filtration and washed with approximately 1 ml of ice cold ethanol per 1 g of CEE HCl product. After the removal of most of the solvent by vacuum filtration, the CEE HCl was removed from the filter and then allowed to dry in a fume hood.

The yield of CEE HCl from this method was 74%, but a total yield of about 80 to 92% (i.e. conversion) is obtainable when the CEE HCl remaining in the filtrate or mother liquor following the initial isolation of CEE HCl is considered. Additionally, the reaction product is 94 to 100% CEE HCl, with any impurities consisting of hydrochlorides of creatine and creatinine. Similar experiments performed with hydrogen chloride introduced directly from a gas cylinder led to yields of CEE HCl of only 48 to 63%.

EXAMPLE 2

Optimization Experiments

Optimization experiments were performed by varying certain parameters of the reaction scheme in Example 1, as described below. A 1.5 mole equivalent of acetyl chloride was added dropwise to anhydrous ethanol to generate the acidified ethanol. Creatine monohydrate was added to the acidified ethanol at a ratio of 1 g:6 ml of ethanol and the reaction medium was heated to 37° C. for 20 hours. The reaction medium was then allowed to cool to 30° C. prior to filtration and the product (filter cake) was washed with ethanol chilled to 0° C. The amount of ethanol used in the wash was on a 1:1 w/v (g/ml) basis with the quantity of creatine monohydrate employed as the starting material. This reaction scheme yielded an 83 to 86% conversion of creatine monohydrate to CEE HCl.

A. Length of Reaction Time

Shortening the reaction time from 20 hours to 10–12 hours resulted in a decrease in the conversion of creatine monohydrate to CEE HCl to about 76 to 83%. Increasing the reaction time to greater than 20 hours resulted in no significant increase in the conversion of creatine monohydrate to CEE HCl. Such longer reaction times, however, did result in the increased formation of the undesirable product creatinine HCl.

B. Temperature at Filtration

After heating the reaction medium to 37° C. for 20 hours, the reaction medium was cooled to various temperatures prior to filtration. The results of these experiments are summarized in Table 1.

TABLE 1

| Temperature At Filtration | Product Purity | Product Yield |
| --- | --- | --- |
| 30° C. | 99% | 54% |
| 25° C. | 95% | 66% |
| 6° C. | 94% | 79% |

Cooling the filtrate to 6° C. resulted in significantly greater yields compared to either 25° C. or 30° C., but with a relatively slight loss of purity. In each of these experiments, the primary impurity found in the reaction product was creatine HCl.

C. Ratio of Acetyl Chloride to Creatine Monohydrate

The ratio of acetyl chloride to creatine monohydrate was varied to optimize the production of CEE HCl while minimizing the formation of the undesired product creatinine HCl. The amount of acetyl chloride employed was varied between 1.3 and 2.0 mole equivalents and the results of the experiments are summarized in Table 2.

TABLE 2

| Mole equivalents of acetyl chloride | Conversion | Product Purity | Product Yield |
|---|---|---|---|
| 1.3 | 74% | 99% | 37% |
| 1.4 | 84% | 98% | 48% |
| 1.5 | 83–86% | 99% | 54% |
| 1.6 | 86% | 99% | 57% |
| 2.0 | 83% | 93% | 63% |

The only impurity present in the final solid reaction product was creatine HCl when 1.3 to 1.6 mole equivalents of acetyl chloride were employed. Creatinine HCl was the only impurity identified when 2.0 equivalents were employed. These results indicate that 1.5 to 1.6 equivalents of acetyl chloride may be optimal as these conditions produced the greatest conversion and yield of the desired product with a high degree of purity. Higher amounts of acetyl chloride, such as greater than 2.0 mole equivalents, are less desirable despite the higher yields because of the greater production of the undesired creatinine HCl reaction byproduct.

D. Composition of Starting Ethanol

The composition of the starting ethanol to which the acetyl chloride is added was varied between a 100:0 and 80:20 ratio (v/v) of ethanol (EtOH) to ethyl acetate (EtOAc). The results of these experiments are presented in Table 3.

TABLE 3

| EtOH:EtOAc (v/v) | Conversion | Product Purity | Product Yield |
|---|---|---|---|
| 100:0 | 83–86% | 99% | 54% |
| 95:5 | 88% | 96% | 65% |
| 90:10 | 87% | 93% | 64% |
| 80:20 | 84% | 93% | 64% |

These data indicate that the 95:5 EtOH:EtOAc ratio (v/v) may be preferred because the increase in yield likely outweighs the slight loss in purity. One notable disadvantage with using larger amounts of EtOAc is that the reaction impurities consisted of about a 3:1 molar ratio of creatinine HCl:creatine HCl. Filtering the reaction mixture at a slightly higher temperature would improve the purity of the isolated CEE HCl, but as noted hereinabove (see part B) such an increase in temperature may result in a concomitant decrease in yield.

Notably, all of the acetyl chloride added to the ethanol is also converted to EtOAc. Therefore the actual ratio of EtOH:EtOAc at the time of creatine monohydrate addition is different than the starting material.

A number of literature and patent references are cited in the foregoing application in order to more fully describe the state of the art to which this invention pertains. The entire disclosure of each of these citations is incorporated by reference herein.

While certain embodiments of the present invention have been described and/or specifically exemplified above, various other embodiments will be apparent to those skilled in the art from the foregoing disclosure. The present invention is, therefore, not limited to such embodiments, but is capable of considerable variation and modification without departing from the scope of the following claims.

What is claimed is:

1. A method of producing an ester of creatine and a lower alcohol, comprising the steps of:

a) providing a reaction medium comprising creatine and said lower alcohol; and b) heating said reaction medium in the presence of an acid catalyst generated in situ, said reaction medium being heated to a temperature between about 35° C. and about 50° C. to yield said ester.

2. The method of claim 1, wherein said acid catalyst is generated by the addition of an acyl halide to said reaction medium.

3. The method of claim 2, wherein said lower alcohol comprises ethanol and said acyl halide comprises acetyl chloride.

4. The method of claim 3, wherein acetyl chloride is added to the reaction medium at a rate such that the temperature of the reaction medium does not exceed 60° C.

5. The method of claim 3, wherein the ratio of creatine to ethanol in said reaction medium is in the range of about 1 gram creatine: 6 to 10 ml acidified ethanol.

6. The method of claim 5, wherein said ratio is 1 gram of creatine: 6 ml acidified ethanol.

7. The method of claim 3, wherein the mole equivalents of acetyl chloride to creatine is in the range of about 1.4–2.0.

8. The method of claim 7, wherein said range of mole equivalents of acetyl chloride to creatine is 1.5–1.6.

9. The method of claim 3, wherein said ethanol is denatured ethanol comprising of about 95% ethanol and about 5% ethyl acetate.

10. The method of claim 1, wherein said heating step is carried out at a temperature in the range of 35° C. and 40° C.

11. The method of claim 1, further comprising the step of purifying the creatine ester product.

12. The method of claim 11, wherein said purification step comprises cooling the reaction mixture to a temperature in the range of about 6° C. to 30° C. to effect crystallization of the reaction product, collecting the crystalline reaction product, washing the reaction product, and drying to obtain a purified ester of creatine and said lower alcohol.

13. The method of claim 12, wherein said temperature of the cooled reaction is in the range of about 6° C. and 25° C.

14. The method of claim 13, wherein said temperature of the cooled reaction is about 6° C.

15. The method of claim 12, wherein collection of the crystalline reaction product is performed by filtration.

16. The method of claim 11, wherein said purification step comprises crystallization of the reaction product from ethanol at 35–60° C.

17. The method of claim 10, wherein the reaction medium is heated for about 20 hours.

* * * * *